United States Patent
Ruflin et al.

(10) Patent No.: US 10,201,698 B2
(45) Date of Patent: Feb. 12, 2019

(54) SYSTEMS AND METHODS FOR THE TREATMENT OF ORAL AND SYSTEMIC MALADIES IN ANIMALS USING ELECTRICAL CURRENT

(71) Applicant: ANIMAL ORALECTRICS LLC, Cleveland, OH (US)

(72) Inventors: Paul L Ruflin, Gates Mills, OH (US); Michael J Keller, Tallmadge, OH (US); Michael V Kaminski, Elyria, OH (US); Scott Mizer, Lakewood, OH (US); Robert Armstrong, Solon, OH (US)

(73) Assignee: Animal Oralectrics LLC, Cleveland, OH (US)

( * ) Notice: Subject to any disclaimer, the term of this patent is extended or adjusted under 35 U.S.C. 154(b) by 0 days.

(21) Appl. No.: 15/638,903

(22) Filed: Jun. 30, 2017

(65) Prior Publication Data
US 2017/0296809 A1 Oct. 19, 2017

Related U.S. Application Data

(63) Continuation of application No. 14/591,629, filed on Jan. 7, 2015.
(Continued)

(51) Int. Cl.
  *A61N 1/05* (2006.01)
  *A61N 1/20* (2006.01)
  (Continued)

(52) U.S. Cl.
  CPC ............. *A61N 1/0548* (2013.01); *A61D 5/00* (2013.01); *A61N 1/205* (2013.01); *A61N 1/36014* (2013.01)

(58) Field of Classification Search
  CPC .................................................. A61N 1/0548
  See application file for complete search history.

(56) References Cited

U.S. PATENT DOCUMENTS

| 1,389,662 A | 9/1921 | Irwin |
| 2,103,083 A | 12/1937 | Lynch |

(Continued)

FOREIGN PATENT DOCUMENTS

| EP | 0599786 | 6/1994 |
| EP | 1053675 | 11/2000 |

(Continued)

OTHER PUBLICATIONS

Connelly, K., Animal Oralectrics prevents oral diseases in animals easily and painlessly. Fresh Water Cleveland Website, accessed on Aug. 16, 2017, http://www.freshwatercleveland.com/innovationnews/oralectrics121913.aspx, 2 pages.
(Continued)

*Primary Examiner* — Carl H Layno
*Assistant Examiner* — Jennifer Ghand
(74) *Attorney, Agent, or Firm* — Smith Keane LLP (57) ABSTRACT

Systems and methods for the concurrent treatment of multiple oral diseases and defects while promoting general oral hygiene utilizing electricity are provided for non-human animals. Electrodes are used to deliver an electrical current to the gingival tissues of a mouth in order to achieve a number of therapeutic, prophylactic, and regenerative benefits. These benefits include killing oral microbes, increasing oral vasodilation, reducing oral biofilm, improving oral blood circulation, reversing oral bone resorption, promoting oral osteogenesis, treating gum recession, and fostering gingival regeneration. Other benefits include the treatment of gingivitis, periodontitis, and oral malodor, and other systemic diseases correlated with oral pathogens.

17 Claims, 5 Drawing Sheets

Related U.S. Application Data (60) Provisional application No. 61/924,381, filed on Jan. 7, 2014.

(51) Int. Cl.
  *A61N 1/36* (2006.01)
  *A61D 5/00* (2006.01)

(56) References Cited

U.S. PATENT DOCUMENTS

| | | |
|---|---|---|
| 2,151,738 A | 3/1939 | Buhse |
| D119,035 S | 2/1940 | Lindgren |
| 3,118,450 A | 1/1964 | Freeman et al. |
| 3,207,161 A | 9/1965 | Dietz |
| 3,215,139 A | 11/1965 | Dietz |
| 3,380,446 A | 4/1968 | Martin |
| 3,403,684 A * | 10/1968 | Stiebel ............... A61N 1/0512 331/111 |
| 3,502,076 A | 3/1970 | Bertolini |
| 4,153,060 A | 5/1979 | Korostoff et al. |
| 4,175,565 A | 11/1979 | Chiarenza et al. |
| D256,958 S | 9/1980 | Markham |
| 4,244,373 A | 1/1981 | Nachman |
| 4,378,007 A | 3/1983 | Kachadourian |
| 4,509,519 A | 4/1985 | Detsch |
| 4,802,444 A * | 2/1989 | Markham ............. A01K 13/00 119/709 |
| D307,339 S | 4/1990 | Markham et al. |
| D308,122 S | 5/1990 | Markham et al. |
| 4,924,811 A | 5/1990 | Axelrod |
| 4,924,880 A | 5/1990 | O'Neill et al. |
| 5,034,847 A | 7/1991 | Brain |
| 5,131,383 A | 7/1992 | Juarez |
| 5,207,231 A | 5/1993 | Fakhri |
| RE34,352 E | 8/1993 | Markham et al. |
| 5,263,436 A | 11/1993 | Axelrod |
| D344,161 S | 2/1994 | Markham |
| D349,786 S | 8/1994 | Markham |
| 5,339,771 A | 8/1994 | Axelrod |
| 5,372,501 A | 12/1994 | Shalvi |
| 5,433,735 A | 7/1995 | Zanakis et al. |
| 5,490,520 A | 2/1996 | Schaefer et al. |
| D368,339 S | 3/1996 | O'Rourke et al. |
| 5,496,256 A | 3/1996 | Bock et al. |
| 5,725,377 A | 3/1998 | Lemler et al. |
| 5,741,500 A | 4/1998 | Yates |
| 5,792,067 A | 8/1998 | Karell |
| 5,832,877 A | 11/1998 | Markham |
| 5,857,431 A | 1/1999 | Peterson |
| 5,865,146 A | 2/1999 | Markham |
| D407,868 S | 3/1999 | Axelrod |
| 5,947,061 A | 9/1999 | Markham et al. |
| 6,067,941 A * | 5/2000 | Axelrod ............... A01K 15/026 119/707 |
| 6,212,435 B1 | 4/2001 | Lattner et al. |
| 6,212,535 B1 | 4/2001 | Weikart et al. |
| 6,254,391 B1 | 7/2001 | Darnell |
| 6,265,391 B1 | 7/2001 | Herbert |
| 6,402,683 B1 | 6/2002 | Marty |
| 6,405,681 B1 | 6/2002 | Ward |
| 6,415,740 B1 | 7/2002 | Curry |
| 6,439,166 B1 | 8/2002 | Markham |
| D462,487 S | 9/2002 | Axelrod |
| 6,546,896 B1 | 4/2003 | Markham |
| 6,615,766 B1 | 9/2003 | Curry |
| D504,748 S | 5/2005 | Jager |
| 7,044,737 B2 | 5/2006 | Fu |
| 7,087,260 B2 | 8/2006 | Axelrod |
| 7,111,587 B2 | 9/2006 | Rautenbach |
| 7,118,377 B2 | 10/2006 | Inoue et al. |
| 7,163,399 B2 | 1/2007 | Kajimoto et al. |
| D539,430 S | 3/2007 | Lowsky, Jr. et al. |
| RE39,563 E | 4/2007 | Markham |
| D544,655 S | 6/2007 | Hass |
| RE40,430 E | 7/2008 | Markham |
| D579,157 S | 10/2008 | Edwards |
| 7,600,488 B2 * | 10/2009 | Mann ............... A01K 15/026 119/710 |
| 7,640,894 B2 | 1/2010 | Jager |
| 7,775,795 B2 | 8/2010 | Khawaled et al. |
| D626,706 S | 11/2010 | Ragonetti |
| 7,874,294 B2 | 1/2011 | Burger |
| 7,886,398 B2 | 2/2011 | Morita et al. |
| 7,917,223 B2 | 3/2011 | Madjar et al. |
| D638,589 S | 5/2011 | Axelrod et al. |
| 8,060,220 B2 | 11/2011 | Liebergesell et al. |
| D658,825 S | 5/2012 | Wolfe, Jr. et al. |
| 8,225,747 B2 | 7/2012 | Markham et al. |
| 8,276,547 B2 | 10/2012 | Markham |
| D677,439 S | 3/2013 | Renforth |
| 8,393,300 B2 | 3/2013 | Markham et al. |
| 8,479,750 B2 | 7/2013 | Schaefer et al. |
| D688,836 S | 8/2013 | Costello |
| D689,155 S | 9/2013 | Jahns |
| 8,660,669 B2 | 2/2014 | Nemeh |
| 2001/0012608 A1 | 8/2001 | Darnell |
| 2003/0079693 A1 * | 5/2003 | Jager ............... A01K 15/026 119/707 |
| 2004/0137118 A1 | 7/2004 | Axelrod |
| 2004/0186418 A1 | 9/2004 | Karashima |
| 2005/0037311 A1 | 2/2005 | Bergersen |
| 2005/0203587 A1 | 9/2005 | Liebergesell |
| 2006/0178703 A1 | 8/2006 | Huston et al. |
| 2006/0201446 A1 | 9/2006 | Edwards |
| 2006/0271148 A1 | 11/2006 | Liebergesell et al. |
| 2007/0203389 A1 | 8/2007 | Bergman |
| 2007/0224572 A1 | 9/2007 | Jon |
| 2007/0224898 A1 | 9/2007 | DeAngelis et al. |
| 2007/0259316 A1 | 11/2007 | Conrad et al. |
| 2008/0003540 A1 | 1/2008 | Khawaled et al. |
| 2008/0063703 A1 | 3/2008 | Gross et al. |
| 2008/0233541 A1 | 9/2008 | De Vreese et al. |
| 2008/0280248 A1 | 11/2008 | Pitts et al. |
| 2008/0314333 A1 | 12/2008 | Hurwitz |
| 2009/0117513 A1 | 5/2009 | Nemeh et al. |
| 2010/0224138 A1 | 9/2010 | Axelrod et al. |
| 2011/0009692 A1 | 1/2011 | Gross |
| 2011/0039226 A1 | 2/2011 | Armanino |
| 2011/0117515 A1 | 5/2011 | Jablow |
| 2011/0179851 A1 | 7/2011 | MacK et al. |
| 2011/0230931 A1 | 9/2011 | Hagege |
| 2011/0289707 A1 | 12/2011 | Schaefer et al. |
| 2012/0156648 A1 | 6/2012 | Kaufman et al. |
| 2012/0256750 A1 | 10/2012 | Novak |
| 2012/0272922 A1 | 11/2012 | Axelrod et al. |
| 2013/0072851 A1 | 3/2013 | Doll et al. |
| 2013/0209964 A1 | 8/2013 | Nemeh et al. |
| 2014/0093832 A1 * | 4/2014 | Nemeh ............... A61C 19/063 433/1 |

FOREIGN PATENT DOCUMENTS

| | | |
|---|---|---|
| EP | 1525857 | 4/2005 |
| WO | 1979/001082 | 12/1979 |
| WO | 1992/005753 | 4/1992 |
| WO | 2005/062710 | 7/2005 |
| WO | 2006/018525 | 2/2006 |

OTHER PUBLICATIONS

European Patent Office Search Report and Written Opinion, dated Aug. 16, 2017, International Application No. PCT/US2015/010477 filed Jan. 7, 2015.

Matsunaga, T. et al., Electrode System for the Determination of Microbial Populations, Applied and Environmental Microbiology, vol. 37 No. 1, Jan. 1979, p. 117-121.

Caubet, R., et al., A Radio Frequency Electric Current Enhances Antibiotic Efficacy . . . , Antimicrobial Agents and Chemotherapy, vol. 48, No. 12, Dec. 2004, pp. 4662-4664.

Giladi, M., et al., Microbial Growth Inhibition by Alternating Electric Fields, Antimicrobial Agents and Chemotherapy, vol. 52, No. 10, Oct. 2008, pp. 3517-3522.

(56) References Cited

OTHER PUBLICATIONS

Del Pozo, J.L., et al., The Electricidal Effect is Active in an Experimental Model . . . , Antimicrobial Agents and Chemotherapy, vol. 53, No. 10, Oct. 2009, pp. 4064-4068.
Del Pozo, J.L., et al., Effect of Electrical Current on the Activities of Antimicrobial Agents . . . Antimicrobial Agents and Chemotherapy, vol. 53, No. 1, Jan. 2009, pp. 35-40.
Del Pozo, J.L., et al., The Electricidal Effect: Reduction of *Staphylococcus* . . . , Antimicrobial Agents and Chemotherapy, vol. 53, No. 1, Jan. 2009, pp. 41-45.
Davidovitch, Z., et. al., Effect of electric currents on gingival cyclic nucleotides in vivo (Abstract). Journal of Periodontal Research, 1980, 15: 353-362.
Hashimoto, H., Effect of micro-pulsed electricity on experimental tooth movement (Abstract). Nihon Kyosei Shika Gakkai Zasshi, Aug. 1990, 49(4):352-61.
Horning, GM., et al., The prevalence of periodontitis in a military treatment problem (Abstract). J Am Dent Assoc., Nov. 1990, 121(5):616-22.
Onkormanyzat, F., et al., The use of iontophoresis in dental practice (Abstract). Fogorv Sz. Jun. 1993, 86(6):205-12.
Wang, Q., et al., Osteogenesis of electrically stimulated bone cells mediated in part by calcium ions (Abstract), Clin Orthop Relat Res. Mar. 1998, (348):259-68.
Davidovitch, Z, et al., Electric currents, bone remodeling, and orthodontic tooth movement. II. Increase in rate of tooth . . . (Abstract), Am J Orthod, Jan. 1980, 77(1):33-47.
Buch, F., et al., Direct current influence on bone formation in titanium implants (Abstract). Biomaterials, Nov. 1984, 5(6):341-6.
Puhar, I., et al., Efficacy of electrical neuromuscular stimulation in the treatment of chronic periodontitis. J Periondontal Implant Sci 2011; 41:117-122.
Bolton, L., et al., Direct-Current Bactericidal Effect on Intact Skin. Antimicrobial Agents and Chemotherapy, Jul. 1980, vol. 18, No. 1, pp. 137-141.
Ehrlich, G.D., et al., Engineering Approaches for the Detection and Control of Orthopaedic Biofilm Infections, Clin Orthop Relat Res. Aug. 2005, (437):59-66.
Matl, FD., et al., Augmentation of antibiotic activity by low-frequency electric . . . (Abstract). Bioelectromagnetics, Jul. 2011, 32(5):367-77.
Sandhu, SP., et al., Comparative evaluation of different strengths of electrical current . . . (Abstract). Indian J Dent Res. Apr.-Jun. 2010; 21(2):207-12.
Kaynak, D., et al., A histopathologic investigation on the effects of electrical stimulation . . . (Abstract). J Periodontol, Dec. 2005, 76(12):2194-204.
Hagiwara, T., et al., Effect of electrical stimulation on mandibular distraction osteogenesis (Abstract). J Craniomaxillofac Surg, Feb. 2000, 28(1):12-9.
Chakkalakal, DA., et al., Electrophysiology of direct current stimulation of fracture . . . (Abstract). IEEE Trans Biomed Eng., Nov. 1990, 37(11):1048-58.
Kane, WJ. Direct current electrical bone growth stimulation for spinal fusion (Abstract). Spine (Phila Pa 1976), Mar. 1988, 13(3):363-5.
Periodontal Disease Fact Sheet, American Academy of Periodontology, www.perio.org/newsroom/periodontal-disease-fact-sheet, Oct. 10, 2013.
manuelderegil@xxxxxxxxx. "Perioprotect ripoff", perioprotect. ripoff, Mar. 20, 2009.
Petersen, P.E., et al., Strengthening the prevention of periodontal disease: the WHO approach, J Periodontal, Dec. 2005, vol. 76, No. 12, pp. 2187-2193.
Pitman, S., US Army develops tooth-cleaning gum, Cosmetics design.com, Dec. 21, 2005.
Bloomberg Businessweek, Why P&G's Smile is So Bright, Jul. 31, 2002, 4 pages.
Hitti, M., 9 Risk Factors for Tooth Loss, WebMD.com, Nov. 11, 2005, 3 pages.
American Dental Association, Key Dental Facts, Sep. 2008, 26 pages.
Karolefski, J., Changing Habits. Supermarket News., Feb. 16, 2009, http://supermarketnews.com/print/nonfood/changing-habits, 4 pages.
Dental Managment:Cost of Deep Perio Cleaning from a Dentist . . . Oct. 10, 2013, http://thewealthydentist.com/SurveyResults/119-Perio-Cleaning.htm, 2 pages.
Johnsen, M., 2009 Hot Products: Editor's Picks. Drug Store News, Jun. 2009, www.drugstorenews.com, 17 pages.
Ichimura, K., et al., Effect of weak electric current on reducing oral bacteria in vitro. Bull. Tokyo dent. Coll., vol. 42, No. 2, pp. 97-100, May 2001.
Poortinga, A.T., et al., Electric field induced desorption of bacteria from a conditioning film covered substratum. Biotechnology and Bioengineering, vol. 76(4):395-99 Dec. 2001.
Glazer, P.A., et al., Electricity: The history and science of bone growth stimulation for spinal fusion. The Orthopaedic Journal at Harvard Medical School, 2002, pp. 63-67.
Albandar, J.M., et al., Gingival recession, gingival bleeding, and dental calculus in adults 30 years of age and older . . . J Periodontol, Jan. 1999, vol. 70, No. 1, pp. 30-43.
Banga, A.K., et al., Iontophoresis and electroporation: comparisons and contrasts. International Journal of Pharmaceutics 179 (1999) pp. 1-19.
Piekarski, K., et al., Osteogenetic stimulation by externally applied DC current. Acta Orthop. Scand. vol. 49, pp. 113-120, 1978.
Hartshorne, E. On the causes and treatment of pseudarthrosis and especially that form of it sometimes called supernumerary joint. Am J Med, Jan. 1841; vol. 1; pp. 121-156.
Tronstad et al., "Effect of Electric Current and Silver Electrodes on Oral Bacteria", Endod Dent Traumatol 1985; 1:112-115.
Guthmiller et al., Chapter 8—Peridontal Diseases (pp. 1-19), Polymicrobial Disease, (Washington (DC); ASM Press; 2002).
Gaitte-Jardim Junior et al, "Microbiota Associated with Chronic Osteomyelitis of the Jaw," Brazilian Journal of Microbiology, vol. 41, No. 4, Sao Paulo, Oct. /Dec. 2010.
Han et al., "Term Stillbirth Caused by Oral Fusobacterium nucleatum," Obstetrical Gynecology, 2010, 115: 442-5.
Hintao et al., "The Microbiological Profiled of Saliva, Supragingival and Subgingival Plaque and Dental Caries in Adults with and without Type 2 Diabetes Mellitus," Oral Microbiology Immunology, 2007: 22: 175-181.
International Search Report and Written Opinion of the ISA, dated Apr. 23, 2015, International Application No. PCT/US2015/010477 filed Jan. 7, 2015.
Office Action dated Jun. 15, 2016, U.S. Appl. No. 14/591,629, filed Jan. 7, 2015.
Office Action dated Jan. 3, 2017, U.S. Appl. No. 14/591,629, filed Jan. 7, 2017.
Office Action dated Jan. 3, 2017, U.S. Appl. No. 15/583,194, filed May 1, 2017.

\* cited by examiner

SYSTEMS AND METHODS FOR THE TREATMENT OF ORAL AND SYSTEMIC MALADIES IN ANIMALS USING ELECTRICAL CURRENT

RELATED APPLICATIONS

This application is a continuation of copending U.S. patent application Ser. No. 14/591,629, now abandoned, filed 7 Jan. 2015, entitled "Systems and Methods for the Treatment of Oral and Systemic Maladies in Animals Using Electrical Current," which claims the benefit of provisional patent application Ser. No. 61/924,381, filed 7 Jan. 2014, and entitled "Systems and Methods for the Treatment of Oral and Systemic Maladies in Animals Using Electrical Current," all such patent applications being incorporated herein by reference in their entireties.

BACKGROUND

This invention relates to a method of concurrently promoting general oral hygiene in non-human animals, treating periodontal diseases such as gingivitis and periodontitis, killing oral microbes including cavity-causing bacteria, reducing oral biofilms, increasing blood flow in oral tissues, increasing salivation, promoting gingival tissue regeneration, fostering osteogenesis in the boney structures of the teeth, mouth and related areas, treating systemic diseases associated with oral bacteria, and treating other periodontal and oral maladies through the non-invasive application of weak direct current electricity to the surfaces in the oral cavity, and it also relates to an apparatus suitable for providing direct current electricity for these therapeutic, prophylactic, and regenerative effects.

Periodontal disease has been identified as a risk factor for various systemic diseases by dentists, physicians, and veterinarians. Included in these diseases are cardiovascular disease, adverse pregnancy outcomes, and diabetes with newfound evidence supporting its association with pancreatic diseases and arthritis. While many of the studies establish correlation between the presence of periodontal disease and these systemic conditions, causation, with most of these conditions, is still a subject of ongoing research. A few of the biological mechanisms which have been proposed as to how oral bacteria stemming from periodontal disease can cause systemic disease are as followed:

1. Direct effect of oral infections: Oral microbes and their byproducts can gain systemic access via the circulatory system through traveling through compromised tissue and inflamed periodontium in the oral cavity. In gaining systemic access, oral microbes have the potential to directly influence subclinical mediators of various systemic diseases.

2. Inflammation: People with periodontal disease have elevated levels of systemic inflammatory markers due to the burden of increased levels of oral bacteria. Treatment for periodontal disease has been reported to decrease systemic inflammation levels.

3. Cross-reactivity: The progression of systemic diseases can be accelerated by the immune response to bacterial heat-shock proteins creating antibodies that cross-react with innate heat shock proteins expressed on cells of the damaged tissues.

SUMMARY OF THE INVENTION

The present invention relates to an apparatus for aiding overall oral health of a non-human animal, and more particularly to treating periodontal diseases such as gingivitis and periodontitis, killing oral microbes including cavity-causing bacteria, reducing oral biofilms, increasing blood flow in oral tissues, increasing salivation, promoting gingival tissue regeneration, fostering osteogenesis in the boney structures of the teeth, mouth and related areas, treating systemic diseases associated with oral bacteria, and treating other periodontal and oral maladies through the non-invasive application of weak direct current electricity to the surfaces in the oral cavity.

One aspect of the present invention includes a device including a body extending along a longitudinal axis between a first end and an opposite second end, the body having an external surface comprising a plurality of circumferential ridges located between the first end and the second end and extending annularly about the longitudinal axis, the body at least partially surrounding a first cavity, the first cavity at least partially bounded by a terminus contained within the body, the terminus intersecting the longitudinal axis; a first electrically conductive surface forming a first portion of the external surface, the first electrically conductive surface extending annularly around a first portion of a first circumferential ridge of the plurality of circumferential ridges at a first longitudinal location along the longitudinal axis; a second electrically conductive surface forming a second portion of the external surface, the second electrically conductive surface extending annularly around a second portion of the first circumferential ridge of the plurality of circumferential ridges at the first longitudinal location; and a power source disposed in the first internal cavity; wherein the first electrically conductive surface is in electrical communication with a first pole of the power source and the second electrically conductive surface is in electrical communication with a second pole of the power source.

The body of the device may at least partially have an hourglass shape. Further, the first electrically conductive surface may be disposed on a first plurality of the circumferential ridges, and the second electrically conductive surface may be disposed on a second plurality of the circumferential ridges.

The first plurality of the circumferential ridges of the device may be the same as the second plurality of the circumferential ridges. Additionally, the external surface may have an electrically insulative portion disposed between the first electrically conductive surface and the second electrically conductive surface, and the electrically insulative portion may be formed from an elastomeric material having a first durometer hardness and the first and second electrically conductive surfaces having a second durometer hardness. The first durometer hardness may be substantially the same as the second durometer hardness.

The body of the device may extend longitudinally along a length between the first end and the second end, wherein the first cavity extends through the first end and towards the second end, the device may further have a second cavity extending through the second end towards the first end, the first cavity and the second cavity being separated by a divider forming the terminus of the first cavity. One of the first cavity and the second cavity may be longer than one half of the length.

The first conductive surface and the second conductive surface of the device may be electrically coupled through a load resistance of up to about 70 kilo-ohms, an electrical current of between 50 microamps and 500 microamps will flow through the load resistance. Additionally or alternatively, the electrical current may about 50 microamps to about 250 microamps, and/or the electrical current may be about 100 microamps.

DETAILED DESCRIPTION

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

It is known in the art that oral bacteria cannot survive when exposed to low-microampere direct current electricity. This method of killing oral bacteria and treating bacteria-caused conditions such as gingivitis has been demonstrated in Nachman, U.S. Pat. No. 4,244,373 of Jan. 13, 1981 and in Detsch, U.S. Pat. No. 4,509,519 of Apr. 9, 1985. Killing oral bacteria has the added benefit of preventing tooth decay and dental caries, or cavities. Generally, tooth decay is attributed to aerobic acid-producing bacteria whose acid causes uncompensated demineralization of the teeth. However, Nachman does not instruct optimal approaches to reducing oral bacteria including aerobic and anaerobic bacteria on a species-by-species level and instead teaches a generic, untargeted treatment.

It has been discovered that by delivering a current level in the approximate range of 50 to 250 microamperes, a direct current electrical treatment is able to deliver new and unexpected therapeutic, prophylactic, and regenerative benefits previously unknown in the art.

Specifically, by utilizing a direct current in the aforementioned range, not only can such a treatment kill bacteria, but it can also kill or disable viruses and fungus as well. Studies from the podiatric field have shown that higher current levels than those used in existing oral electrical treatments are necessary to effectively treat fungal infections ("Low-Voltage Direct Current as a Fungicidal Agent for Treating Onychomycosis", Kalinowski, et al., Journal of the American Podiatric Medical Association Vol. 94 No. 6: 565-572, 2004). Thus, fungicidal and viricidal benefits have been additionally provided in conjunction with a method already known to be bactericidal. Studies have shown that these microbicidal properties begin to take effect within approximately 5 and 15 minutes of treatment, reducing both supra- and sub-gingival microbes.

In addition, clinical research has demonstrated that a direct current in the approximate range of 50 to 250 microamperes was able to regenerate gingival tissues, providing a non-surgical treatment alternative for those with recessed gums. While the osteogenic properties of electricity have been known in the art, the connection between nonosseous tissue regeneration and electricity were not well known in the art prior to these experiments. The unique current range associated with the method and apparatus of this invention is one of a few effective methods in animal the dental field to accomplish effective gingival tissue regeneration in a non-surgical manner.

In further research, testing has examined the effects of direct current stimulation on three different oral bacteria (*F. nucleatum, S. oralis, P. gingivalis*) in both saline and saliva solutions. This testing varied the current levels, inoculum size of bacteria, solution medium, and treatment time to develop an optimal treatment to reduce these three bacteria species associated with both periodontal and systemic diseases.

The results of this testing showed that each different bacterium had a different dose response to DC stimulation. Through this testing, treatment parameters have been identified that were able to kill up to 100% of *S. oralis*, 99.1% of *F. nucleatum*, and 52.3% of *P. gingivalis* in a single treatment lasting thirty minutes or less. This research yielded specifications for DC-based treatments of targeted pathogens that was previously unknown in the art. The optimal treatment parameters discovered in this research and described in this method can provide an innovative way to reduce these three species of bacteria, in both supra- and sub-gingival environments, and thus prevent and/or treat their associated complications including periodontal disease, biofilm formation, as well as the systemic diseases correlated to these oral pathogens.

In addition, scanning electron microscopy (SEM) has been conducted on *F. nucleatum* colonies before and after a 30 minute treatment to better understand the mechanism by which the method according to this invention is able to reduce bacterial levels. The SEM imagery suggested that the method according to this invention interferes with bacterial cellular division and can weaken the outer envelope (cell membrane) resulting in fragile cellular structures that can easily break. It is contemplated that this is phenomenon is an example of electroporation, where the permeability of cellular membranes may be affected by electrical stimulation either temporarily or permanently. It is further contemplated that the electroporation caused by the method according to this invention could play a role in developing new therapies in molecular biology which would take advantage of this cellular permeability and introduce new material into the cells of oral pathogens or oral tissues through mechanisms including, but not limited to genetic material (transfection) such as DNA, RNA, sRNA, siRNA, plasmids, etc. These effects would prove a new tool in targeted gene therapies for oral applications.

Specifically, devices according to the present invention may be used to reduce viable colony forming units (CFU) in various oral bacteria.

Figures 1, 2:
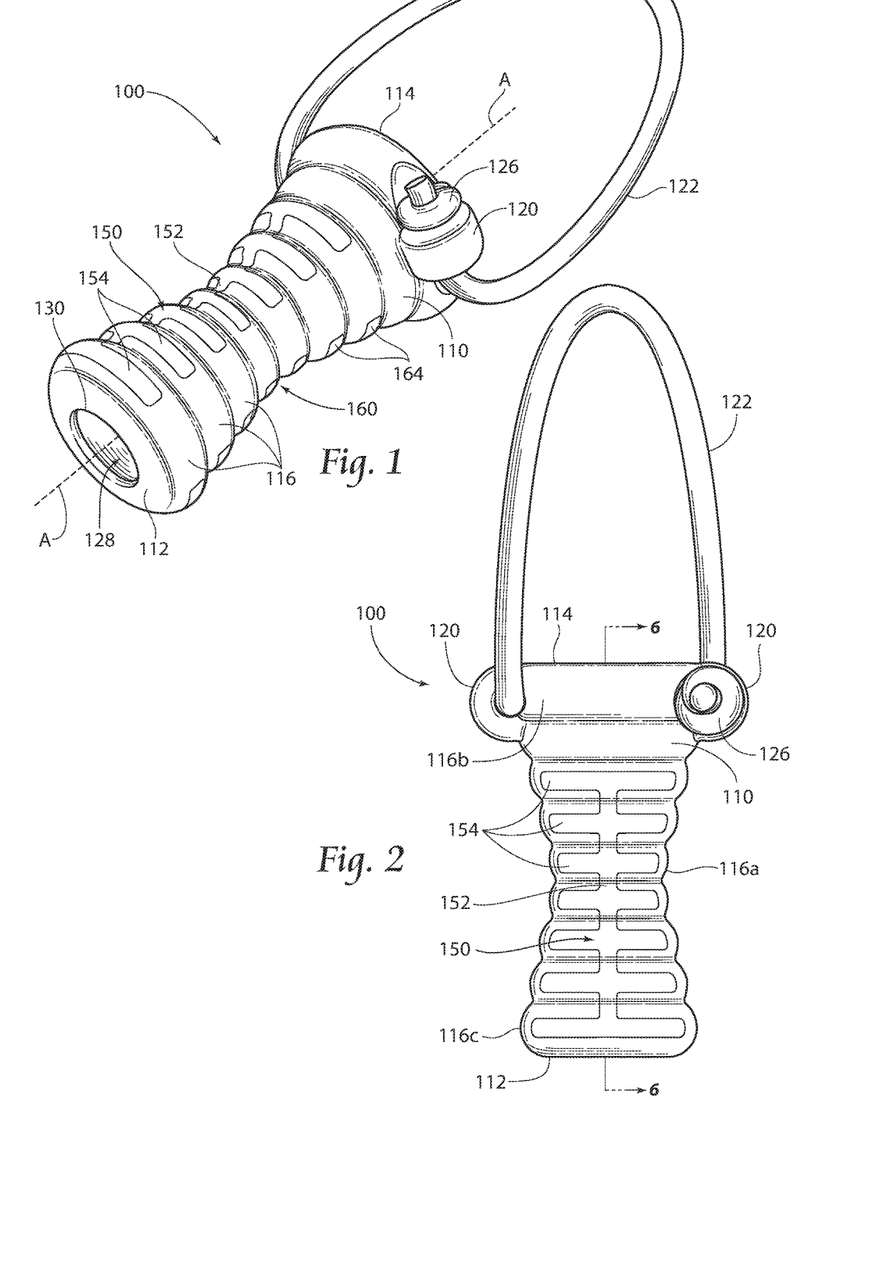
FIG. 1 is a perspective view of a first embodiment of a device according to the present invention.
FIG. 2 is a front elevation view of the embodiment shown in FIG. 1.
Figure 3:
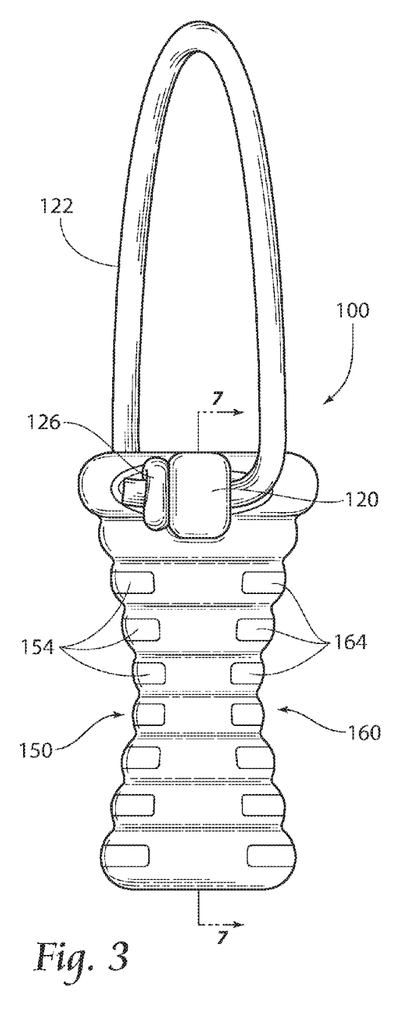
FIG. 3 is a right side elevation view of the embodiment of FIG. 1.
Figure 4:
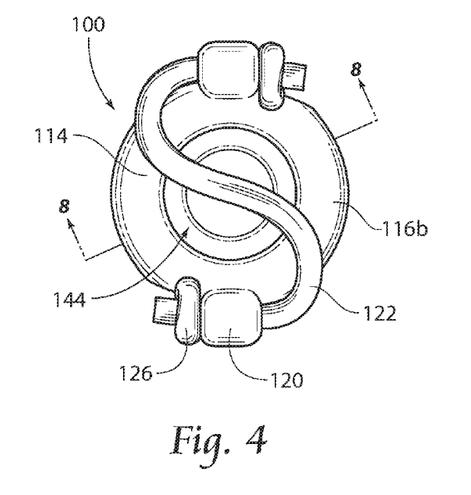
FIG. 4 is a top plan view of the embodiment of FIG. 1.
Figure 5:
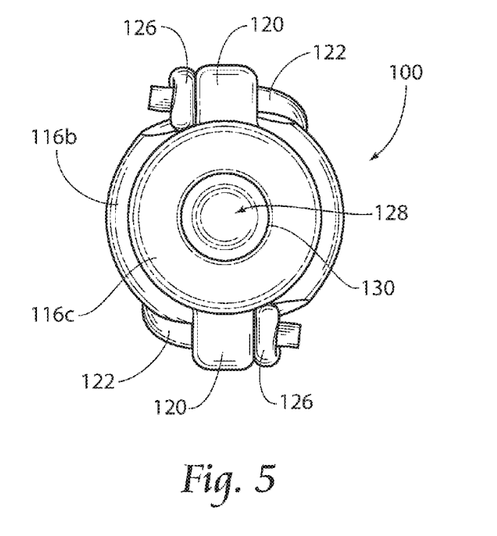
FIG. 5 is a bottom plan view of the embodiment of FIG. 1.
Figures 6, 7, 8:
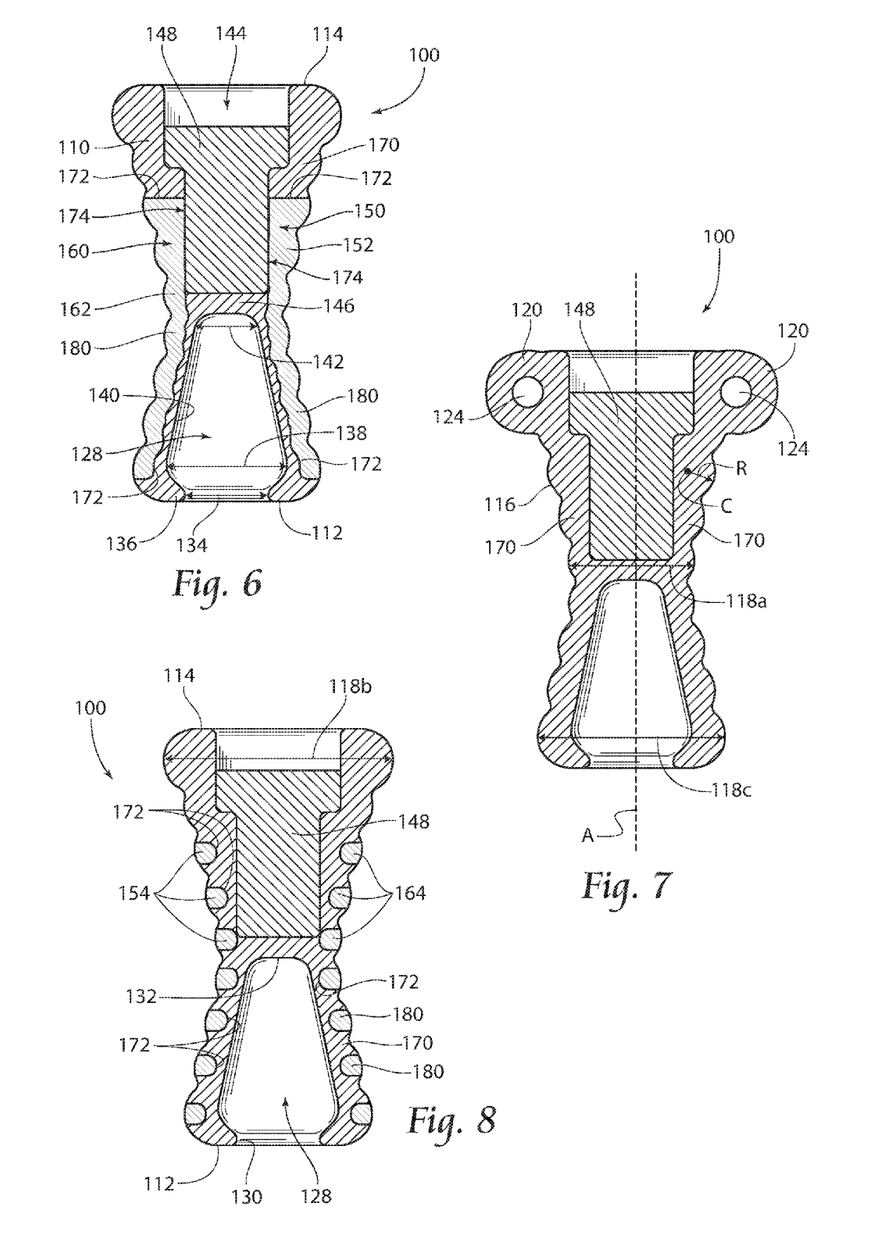
FIG. 6 is a cross-sectional view taken along line 6-6 of FIG. 2.
FIG. 7 is a cross-sectional view taken along line 7-7 of FIG. 3.
FIG. 8 is a cross-sectional view taken along line 8-8 of FIG. 4.

An embodiment 100 of an animal treatment apparatus is shown in FIGS. 1-8. The treatment apparatus 100 generally includes a body 110 extending longitudinally between and including a first end 112 and a second end 114 opposite the first end 112. The body 110 is preferably a general hourglass shape. While the hourglass shape could be provided in a variety of fashions, a preferred structure includes the outward appearance of a plurality (e.g., at least three) of circumferential ridges 116 defined by a plurality of stacked toroids. While the term "toroid" is utilized to describe the general outward appearance of portions of the body 110, it is understood that the internal construction of the body 110 may not include corresponding toroidal configurations. With reference momentarily to FIG. 7, it should be appreciated that the "toroid" language generally describes a ridge 116 having a continuous curved outer surface of a preferred radius R, wherein such radius R extends from a centerpoint C that resides on a circle which extends about a central longitudinal axis A of the body 110. A first circumferential ridge 116a is preferably disposed at or near a longitudinal midpoint of the body 110. This circumferential ridge 116a has a first ridge diameter (118a in FIG. 7), which may be the smallest of any of the ridges 116. A second circumferential ridge 116b is preferably disposed at the second end 114 of the body 110. This circumferential ridge 116b has a second ridge diameter (118b in FIG. 8), which is larger than the first ridge diameter 118a, and it further may be the largest diameter of any of the ridges 116. A third circumferential ridge 116c is preferably disposed at the first end 112 of the body 110. This circumferential ridge 116c has a third ridge diameter (118c in FIG. 7), which is larger than the first ridge diameter 118a, and it may be the same as or smaller than the second ridge diameter 118b.

On the body 110, preferably extending radially outward from the second circumferential ridge 116b may be one or more handle anchors 120. The anchors 120 preferably provide a location at which to, for example, dock a flexible handle 122, such as a rope. The rope 122 may be inserted through the anchor 120, such as through an aperture (124 in FIG. 7) formed at least partially in the anchor 120, and possibly partially into the second circumferential ridge 116b. The rope 122 could then be provided with a slip-stop 126, such as a knot or aglet. Where more than one anchor 120 is provided, the plurality of anchors 120 is preferably equally spaced about a circumference of the body 110 extending about the longitudinal axis A.

One or more cavities may extend inwardly from an exterior surface of the body 110. A first cavity 128 extends into the body 110 from the first end 112. The cavity 128 is preferably formed symmetrically about the longitudinal body axis A, extending into the body 110 for a preferred depth, which may be less than half of the longitudinal length of the body 110, which extends between and includes the first end 112 and the second end 114. The cavity 128 extends from an aperture 130 formed in the first end 112 to a closed end 132 disposed within the body 110. The aperture 130 extends about a diameter 134 defined by an annular ridge 136, and the cavity 128 expands outwardly to a second, larger diameter 138 on the inside of the ridge 136. Extending further inward, the cavity 128 is defined by a substantially frustoconical wall 140, ending with a terminal diameter 142, which is preferably smaller than both the aperture diameter 134 and the larger diameter 138. A second cavity 144 may also be provided in the body 110. The second cavity 144 may extend into the body 110 from the second end 114, and may be provided as a cylindrical or a stepped reentrant bore. The second cavity 144 extends into the body 110 for a preferred depth, but preferably does not extend so far as to intersect the first cavity 128. If the body 110 is provided with a first cavity 128 and a second cavity 144 as described, they are preferably separated by a divider 146, which is preferably a solid, non-conductive divider formed of the same nonconductive material as a majority of the body 110.

At least two electrodes, one cathode 150 and one anode 160, are provided and electrically accessible on the material forming the outer surface of the device 100. On an external surface of at least one of the ridges 116, a cathodic electrode element 150 is provided. On an external surface of at least one of the ridges 116, an anodic electrode element 160 is provided. The body 110 is generally formed from a first, electrically insulative material 170 and a second, electrically conductive material 180. The insulative material 170 may be injection molded from a desirable material in a first mold, which may include a removable insert defining wells 172 to receive the conductive material 180 after the insulative material 170 is cured. The conductive material 180 is placed into electrical communication with the electronics module 148 through one or more connection passages 174. The wells 172 preferably have a radial surface area that is larger than the longitudinal cross-sectional area of the connection passage 174. The conductive material 180 is preferably exposed within the second cavity 144 through the connection passage 174. Alternatively, a wire (not shown) or other electrical connection could be used. Preferably, the conductive material 180 comprises a resilient material (preferably durometer Shore A range of about 25 to about 80, or even up to about 90-95) to encourage chewing of the treatment apparatus 100. As non-limiting examples, a conductive silicone, urethane, fluorosilicone, or other conductive polymer or a conductive fabric (e.g. silver-plated nylon, or non-woven conductive or conductive-through-adhesive fabric tape) may be used as, or as a part of, the covering material. Regardless of the covering material used, it is preferred that at least a portion of the material forming the outer surface of the apparatus conducts electricity from the power supply, or regulated amount thereof, to the animal's mouth. The conductive material portions 180 are preferably separated by non-conductive material 170, such as an insulative polymer (e.g. non-conductive silicone) or fabric, preferably having approximately the same durometer Shore A hardness as the conductive material, or a similar tooth feel thereto. Alternatively, in another preferred embodiment, the hardness of the non-conductive material 170 is less than that of the conductive material 180, such as about half. While the conductive material 180 may be disposed in the wells 172, the device 100 is preferably provided with a substantially or completely imperforate radial outer surface.

The cathodic electrode 150 may be formed into a variety of configurations, but a preferred configuration includes a cathodic stem portion 152, from which one or more cathodic branches 154 extend. The cathodic stem 152 preferably extends along a majority of the length of the body, generally parallel to the longitudinal axis A. The cathodic branches 154 are preferably formed integrally with the stem 152, but preferably extend annularly from the stem 152, more preferably being disposed on the radially outermost surface of respective ridges 116 of the body 110. As indicated, separated from the cathodic electrode 150 by insulative material 170 is an anodic electrode 160. A preferred anodic electrode configuration includes an anodic stem portion 162, from which one or more anodic branches 164 extend. The anodic stem 162 preferably extends along a majority of the length of the body, generally parallel to the longitudinal axis A. The anodic stem 162 may be diametrically opposed from the cathodic stem 152. The anodic branches 164 are preferably formed integrally with the anodic stem 162, but preferably extend annularly from the anodic stem 162, more preferably being disposed on the radially outermost surface of respective ridges 116 of the body 110. A plurality of ridges 116 preferably includes a cathodic branch 154 and an anodic branch 164 on each ridge 116. It should be noted that alternative shapes and configurations that maintain a spaced cathodic electrode 150 and anodic electrode 160 configuration are within the scope of the present invention. For instance, if the device 100 is provided with two anchors 120, which are diametrically opposed from one another, while the electrode stems 152,162 may be disposed longitudinally in line therewith, it is preferred to have the stems 152,162 longitudinally offset by some predetermined number of degrees, such as about 90 degrees, as shown.

Figure 9:
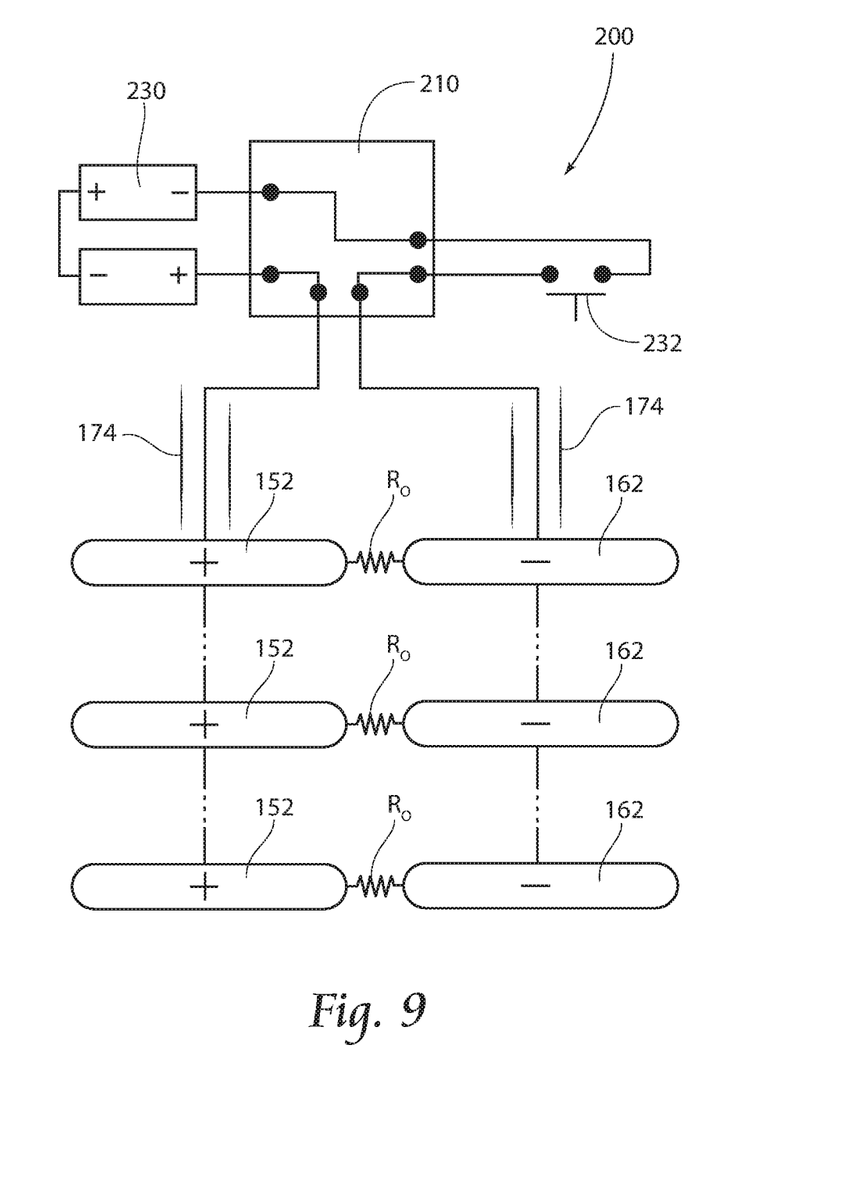
FIG. 9 is a schematic view of an embodiment of an electrical circuit according to the present invention.

Turning now to FIGS. 6-9, disposed within the second cavity 144 may be an electronics module 148, which is preferably sealed water-tight, and houses a circuit 200 shown in FIG. 9. The circuit 200 generally includes a control board 210 and a power supply 230. The control board 210 and power supply 230 may be of any types known to provide an ability to transfer the power of the power supply 230 to the electrodes 150 and 160, which were previously described. Fully contemplated within the purview of the present invention to be included in the circuit 200 are timers, audible (e.g., sounds representative or imitative of a mouse squeak or bird chirp), tactile/haptic (e.g. vibrations provided by a vibratory motor such as a coin or pancake vibration motor), and/or visible prompts or feedback, or usage, activity and/or power indicators (e.g. beeper, buzzer, light-emitting diodes), motion activation (e.g. using an accelerometer), moisture activation, pressure activation, electrical current intensity adjustment (e.g., based on sensed impedance between a cathode 150 and an anode 160), and/or an on/off switch 232 to control the possible current delivery by the power supply 230. Optionally, a programmable microcontroller (or a pre-programmed ASIC) could be used, as previously described, to control the various functions prompts/feedback and could record various treatment parameters and/or treatment history in non-volatile memory to be analyzed in real-time or post-treatment. If a programmable microcontroller is utilized, a programming interface may be provided, such as a wired (e.g., Universal Serial Bus) or a wireless (e.g., Bluetooth®, WiFi (e.g., IEEE 802.11), infrared, etc.) interface to allow programming of the microcontroller, thereby enabling it to control the operation of the device. Parameters that may be desirably programmed may be electrical stimulation intensity (e.g. current level) and/or the frequency and type of prompts and/or feedback. The power supply 230 may be a simple dry-cell battery, a rechargeable battery, a capacitor, a kinetic energy generator, a piezoelectric generator, a microcontrolled DC power supply, or other power supply (such as a microcontrolled AC power supply). Regardless of the power supply 230 used, it is most preferable to control the amount of electrical current delivered by the treatment device to provide a relatively constant current power source to provide up to about 500 microamps of direct or alternating current. While 50 microamps to about 500 microamps may be a desired range, about 50 microamps to about 250 microamps is preferred, and about 100 microamps is still further preferred. Such control may be provided by a microcontroller or discrete monitoring circuitry (such as through current and/or impedance sensing), or optimal dry-cell design if expected impedances are generally known. It is further contemplated by the present invention that the treatment apparatus 100 is preferably used by non-human animals, such as felines, bovines, ovines, canines, equines, porcines, etc. Power supplies and other circuit components may be found in published U.S. patent application Ser. No. 13/839,513, which is incorporated herein by reference in its entirety.

A circuit will be completed by an animal's mouth when the device 100 is masticated. This is schematically represented in FIG. 9 by impedances Ro, provided by the animal's mouth (e.g. saliva and/or oral tissues), extending between two or more electrodes. The circuit 200 contained within the electronics module 148 may be coupled to the conductive material 180 forming the electrodes 150,160 by exposed electrical conductors supported by the module 148 which are placed in frictional contact with the conductive material 180 when the module 148 is inserted into and supported within the second cavity 144. Preferably, electrical conductors that interface between the power supply 230 and the electrodes 150,160 extend from the power supply 230 in the same direction. That is, a first electrical conductor that couples the cathodic electrode 150 to the positive pole of the power supply 230 preferably extends from the positive pole in a first longitudinal or radial direction. A second electrical conductor that couples the anodic electrode 160 to the negative pole of the power supply 230 preferably extends from the negative pole in the same longitudinal or radial direction as the first electrical conductor. Of course, the coupling of the electrodes 150,160 to the power supply 230 is not required to be a direct coupling, but rather may be indirect coupling through a variety of other electrical passive or active electrical components, such as one or more voltage regulators, operational amplifiers, transistors, microcontrollers, voltage converters/inverters, etc. Regardless of the specific circuit design, it is preferable that the circuit 200 be able to supply a stimulation (pulsed or steady) current of about 50 microamps to about 500 microamps to a load (Ro) of up to about 70 kilo-ohms. More preferably, to such load, a stimulation current of about 50-250 microamps, and still more preferably, a current of about 100 microamps has been shown to be effective.

Figure 10:
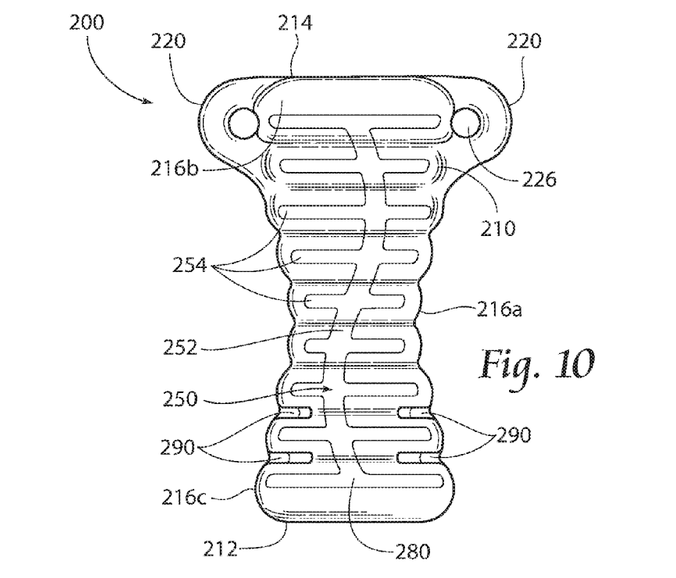
FIG. 10 is a front elevation view of a second embodiment of a device according to the present invention.
Figure 11:
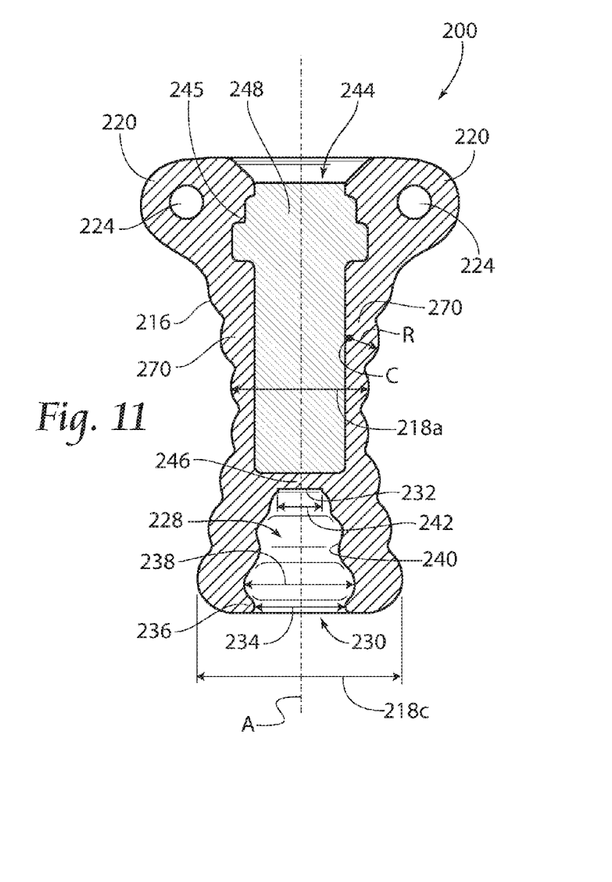
FIG. 11 is a cross-sectional view taken through the center of the embodiment of FIG. 10, parallel to the elevation view of FIG. 10.

FIGS. 10 and 11 depict features of a second embodiment 200 of a device according to the present invention, where similar reference numerals refer to substantially similar or identical structure as described with respect to the first embodiment 100. Like the first embodiment one or more cavities may extend inwardly from an exterior surface of the body 210. A first cavity 228 extends into the body 110 from the first end 212. The cavity 228 is preferably formed symmetrically about the longitudinal body axis A, extending into the body 210 for a preferred depth, which may be less than half of the longitudinal length of the body 210, which extends between and includes the first end 212 and the second end 214. The cavity 228 extends from an aperture 230 formed in the first end 212 to a closed end 232 disposed within the body 210. The aperture 230 extends about a diameter 234 defined by an annular ridge 236, and the cavity 228 expands outwardly to a second, larger diameter 238 on the inside of the ridge 236. Extending further inward, the cavity 228 is defined by a substantially frustoconical wall 240, which may be ribbed or textured, ending with a terminal diameter 242, which is preferably smaller than both the aperture diameter 234 and the larger diameter 238. A second cavity 244 may also be provided in the body 210. The second cavity 244 may extend into the body 210 from the second end 214, and may be provided as a cylindrical or a stepped reentrant bore. The cavity 244 may include a retaining lip 245 adapted to maintain the electronics module 248 generally securely within the cavity 244. The second cavity 244 extends into the body 210 for a preferred depth, which may be greater than half of the length of the body 210 along the axis A, but preferably does not extend so far as to intersect the first cavity 228. If the body 210 is provided with a first cavity 228 and a second cavity 244 as described, they are preferably separated by a divider 246, which is preferably a solid, non-conductive divider formed of the same nonconductive material as a majority of the body 210.

Also like the first embodiment 100, this embodiment 200 includes at least two electrodes, one cathode 250 and one anode 260, provided and electrically accessible on the material forming the outer surface of the device 200. The stem portions 252, (262 not shown) of this embodiment 200 are serpentine, rather than being substantially linear like the stem portions 152,162 on the first embodiment 100. Additionally, this embodiment 200 includes one or more ruts 290 adapted to receive an edible substance (e.g. canned dog food or nutrient gel) or a dentifrice. The ruts 290 preferably extend radially about the body 210 for a predetermined length or about a predetermined angle (e.g. 30-60 degrees) about the axis A.

Treatment of Non-Human Animals

A method according to the present invention may be used for promoting oral hygiene in non-human animals, such as felines, bovines, ovines, canines, porcines, and/or equines. The method comprises the steps of providing a treatment apparatus comprising a power source and a plurality of electrodes electrically coupled to the power source. The power source may be an internal direct current power source, or other power source as described above. The plurality of electrodes includes at least one, but preferably a plurality of cathodic electrodes and at least one, but preferably a plurality of anodic electrodes. The electrodes may be positioned in a spaced arrangement about, and preferably conductive through, the exterior of the treatment apparatus by a conductive material. The electrodes may be arranged in an alternating cathodic/anodic fashion about the device. The method further comprises the step of providing such device to a non-human animal, thereby allowing delivery of electrical current from the power source, through the electrodes and to at least one of the animal's oral secretions (e.g., saliva) and oral tissue (e.g., lingual tissue, dental tissue, gingival tissue, periodontal tissue, and oral mucosa tissue).

Systems and methods according to the present invention may be used to reduce oral bacteria and/or biofilm, as well as to treat systemic diseases that may be associated with oral bacteria, in non-human animals, such as dogs, cats, sheep, horses, cows, pigs, etc.

For instance, periodontal disease is one of the most common health problems affecting dogs (>75%). The prevalence of periodontal disease has been found to increase age but decrease with body weight. Various systemic diseases have been suggested as a strong co-factor for periodontal disease in animals, just as in humans. It has been suggested that periodontal disease could have a causal relationship with systemic diseases in both humans and animals. For dogs, and animals in general, periodontitis is a recurrent and persistent disease and exposes the host to negative systemic effects over an extended period of time, e.g. several years.

It has been observed that, over the course of several years, frequent exposure of bacteremia as a result of minor trauma at sites of periodontal inflammation may cause infection or induce inflammation at distant sites with the body. The pathogenesis of periodontal disease in dogs has been linked with gram-negative anaerobic bacteria upon accumulation within the gingival sulcus causing inflammation and the formation of periodontal pockets. The inflammatory response to periodontal pathogens promotes the formation and release of endotoxins and inflammatory cytokines that can decrease functions of vital organs over time. It has been suggested that systemic diseases may be associated with periodontal disease in dogs, including chronic bronchitis, pulmonary fibrosis, endocarditis, interstitial nephritis, glomerulonephritis, and hepatitis.

Periodontal organisms present in dogs with periodontitis have been isolated and identified previously. For instance, the following periodontal pathogens have been found to be associated with periodontal disease in dogs: *P. gingivalis* (64% of periodontitis-positive dogs), *C. rectus, A. actinomycetemcomitans, P. intermedia, T. forsythensis, F. nucleatum* (4% of periodontitis-positive dogs), *E. corrodens, P. denticanis, P. gulae, P. salivosa*. Recommended treatments using systems and/or methods according to the present invention to treat and/or prevent periodontal disease by reducing or controlling such types of bacteria, may include a predetermined time, such as 20 minutes, of oral secretions and/or tissue (i.e., saliva, lingual tissue, dental tissue, gingival tissue, periodontal tissue, and/or oral mucosa tissue) exposure to an electrical current (alternating or direct current, constant or pulsed) level of between about 50 microamps ($\mu A$) and about 500 microamps ($\mu A$), with about 50 microamps to about 250 microamps being preferred, and about 100 microamps being still further preferred. Devices according to the present invention have been shown to be effective at reducing the count of bacterial species in this current range.

As with dogs, periodontal disease in cats is associated with local inflammation and is purported to influence and induce systemic responses and organ function in distal sites. One of the common oral pathogens found in the oral cavity of cats is *P. gingivalis*. Studies have demonstrated that indeed measureable systemic changes arise during the progression of periodontal disease, such as increased levels of serum IgG. Further, these levels could be altered with periodontal treatment. Recommended treatments using systems and/or methods according to the present invention to treat and/or prevent periodontal disease in cats by reducing or controlling such types of bacteria, may include a predetermined time, such as 20 minutes, of oral tissue exposure to an electrical current (alternating or direct current, constant or pulsed) level of between about 50 microamps ($\mu A$) and about 500 microamps ($\mu A$), with about 50 microamps to about 250 microamps being preferred, and about 100 microamps being still further preferred. Devices according to the present invention have been shown to be effective at reducing the count of such bacterial species in this current range.

Periodontitis may also be found in sheep and cattle, also referred to as "broken mouth", and is associated with severe degradation of periodontal collagen, loss of alveolar bone, appearance of periodontal pockets and premature tooth loss. Although morphological and histological differences exist between the periodontium of sheep, cattle, and humans, the histopathological appearance is similar in periodontal disease, including the role that *P. gingivalis* plays in the progression of the disease. Recommended treatments using systems and/or methods according to the present invention to treat and/or prevent periodontal disease in sheep and/or cattle by reducing or controlling such types of bacteria, may include a predetermined time, such as 20 minutes, of oral tissue exposure to an electrical current (alternating or direct current, constant or pulsed) level of between about 50 microamps ($\mu A$) and about 500 microamps ($\mu A$), with about 50 microamps to about 250 microamps being preferred, and about 100 microamps being still further preferred. Devices according to the present invention have been shown to be effective at reducing the count of such bacterial species in this current range.

Cardiovascular-related conditions may also exist in non-human animals. For instance, there has in dogs been revealed an association between periodontal disease severity and risk of cardiovascular-related conditions, such as endocarditis and cardiomyopathy. Endocarditis is a result of infection and inflammation of the heart endothelium, or tissue lining the inner surface of the heart valves and can be caused by various microorganisms. Cardiomyopathy is characterized by an enlarged heart that does not function properly. Both diseases carry a poor prognosis based on the severity of the case. For dogs, it has been found that the risk of endocarditis was 6-fold higher in dogs with stage 3 periodontal disease than it was for healthy dogs and for cardiomyopathy it was about 4-fold. Cardiac disease progression may be affected by the presence and/or prevalence of certain oral bacteria, including *S. oralis*, *F. nucleatum*, and *P. gingivalis*. Recommended treatments using systems and/or methods according to the present invention to treat and/or prevent cardiac disease by reducing or controlling such types of bacteria, may include a predetermined time, such as 20 minutes, of oral tissue exposure to an electrical current (alternating or direct current, constant or pulsed) level of between about 50 microamps ($\mu$A) and about 500 microamps ($\mu$A), with about 50 microamps to about 250 microamps being preferred, and about 100 microamps being still further preferred. Devices according to the present invention have been shown to be effective at reducing bacterial burden of all three species in this current range.

In addition to cardiac disease, a prior retrospective longitudinal study has established a relationship between periodontal disease and chronic kidney disease (CKD). The hazard ratio of CKD in dogs, in conjunction with increased serum creatinine and blood urea nitrogen concentrations, has been shown to increase, with increasing severity of periodontal disease, from stage 1 to stage 4, thereby establishing a significant positive association between periodontal disease and CKD.

Both *F. nucleatum* and *P. gingivalis* are common oral pathogens presented in dogs, and may be linked to kidney disease. Accordingly, reduction of such pathogens may be used as a treatment or prevention thereof. Recommended treatments using systems and/or methods according to the present invention to treat and/or prevent kidney disease by reducing or controlling such types of bacteria, may include a predetermined time, such as 20 minutes, of oral tissue exposure to an electrical current (alternating or direct current, constant or pulsed) level of between about 50 microamps ($\mu$A) and about 500 microamps ($\mu$A), with about 50 microamps to about 250 microamps being preferred, and about 100 microamps being still further preferred. Devices according to the present invention have been shown to be effective at reducing the count of such bacterial species in this current range.

Non-human animal diabetes may also be treated and/or prevented using systems and methods according to the present invention. In humans, as stated, there is an established link between diabetes mellitus and periodontal disease, and such a relationship has been suspected in veterinary medicine. One prior study has demonstrated that blood glucose concentrations are increased in relation to attachment loss and periodontal disease state in dogs. Additionally, these levels decreased following periodontal disease treatment.

The *S. oralis* bacterium has been associated with severe periodontitis and diabetes. Recommended treatments using systems and/or methods according to the present invention to treat and/or diabetes by reducing or controlling such types of bacteria, may include a predetermined time, such as 20 minutes, of oral tissue exposure to an electrical current (alternating or direct current, constant or pulsed) level of between about 50 microamps ($\mu$A) and about 500 microamps ($\mu$A), with about 50 microamps to about 250 microamps being preferred, and about 100 microamps being still further preferred. Devices according to the present invention have been shown to be effective at reducing the count of such bacterial species in this current range. Such a reduction may help combat high levels of blood glucose.

Furthermore, systems and methods according to the present invention may be used to affect (preferably reduce and/or eliminate) the number of oral bacteria transferred between animals of different species, such as between a pet and its owner. It is well established that oral bacteria, including periodontal pathogens, can be transmitted between mothers and their children simply through everyday close contact. Therefore, it is not unfounded that transmission of such bacteria may occur between humans and their companion animals. One study investigated In fact, the prevalence of periodontal pathogen species in dogs and their owners to examine the possibility of pet-to-owner transmission has been studied. *P. gulae* was detected in 71.2% of dogs in the study and 16% in the owners. Interestingly, *P. gulae* is extremely uncommon in the human oral cavity, and each owner who harbored the bacteria had a dog that tested positive for the pathogen. Two additional species, *E. corrodens* and *T. denticola*, were found to correlate between owners and dogs indicating that oral bacteria species may be transmitted between dogs and their owners.

The *P. gulae* bacterium, a member of the *Porphyromonas* genus found in the oral cavity of dogs, has been shown to share 60% homology with *P. gingivalis*. This suggests that *P. gulae* would respond similarly to treatment with the device as does *P. gingivalis*. Recommended treatments using systems and/or methods according to the present invention to remedy and/or prevent the transfer of oral bacteria between animals of different species by reducing or controlling such types of bacteria, may include a predetermined time, such as 20 minutes, of oral tissue exposure to an electrical current (alternating or direct current, constant or pulsed) level of between about 50 microamps ($\mu$A) and about 500 microamps ($\mu$A), with about 50 microamps to about 250 microamps being preferred, and about 100 microamps being still further preferred. Either or both animals (e.g. a dog and/or its owner) may be so treated. Devices according to the present invention have been shown to be effective at reducing the count of such bacterial species in this current range. Such treatment should reduce levels of *P. gulae* and diminish the possibility of pathogen transmission to the animal's owner.

The treatment times may be a constant treatment time (e.g. 20 consecutive minutes) or treatments may be prescribed and/or delivered for a predetermined period of time (e.g. 1-60 minutes) within a treatment window (e.g. 24 hours, one week, one month, etc.) in shorter incremental treatments, such as two minutes, five times a day (to achieve 10 minutes of stimulation within a treatment window of 24 hours).

Thus, embodiments according to the present invention are able to achieve multiple prophylactic, therapeutic, and regenerative effects in non-human animals whose combination was not previously known or available in the art. Namely, these effects are: promotion of oral osteogenesis, destruction or disabling of oral microbes, gingival tissue regeneration, reduction and prevention of the formation of oral biofilms, caries prevention, increased oral vasodilation and oral blood flow, treatment of common oral conditions such as gingivitis and periodontitis, treatment of systemic diseases and conditions correlated with oral pathogens, and generally improved oral hygiene.

These effects are accomplished by the delivery of direct current to the animal's oral secretions and/or tissues through a plurality of electrodes. The electrodes may be fashioned out of any electrically-conductive material, including but not limited to metals such as silver, stainless steel, copper, gold, platinum, palladium, aluminum, an alloy thereof, electrically-conductive nanotubes, carbonized rubber, electrically-conductive silicone, or electrically-conductive polymers. The electrodes may be composed of the same or of differing materials.

Electrical conductors then couple these electrodes to an adjustable power supply. All of the anodic electrodes will electrically communicate with the positive pole of the power supply and all of the cathodic electrodes will electrically communicate with the negative pole of the power supply. The adjustable power supply is capable of delivering a stable, direct current in the approximate range of 1 to 500 microamperes. The preferred current setting for most treatments is in the approximate range of 50 to 250 microamperes, with about 100 microamps being still further preferred.

Thus, the reader will see that at least one embodiment herein addresses a desired need in the non-human animal oral hygiene and dental fields to treat common oral diseases and conditions in a more effective, less invasive, and less expensive manner. These embodiments promote general oral hygiene, reduce oral biofilm, treat periodontal diseases such as gingivitis and periodontitis, kill oral microbes including bacteria and thus preventing cavities and tooth decay, increase vasodilation and blood flow in oral tissues, promote gingival tissue regeneration, foster osteogenesis in the boney structures of the teeth, mouth, and related areas, treat systemic diseases related to oral pathogens, and treat other periodontal and oral maladies through the non-invasive application of weak direct current electricity to the surfaces in the oral cavity.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A device comprising:
   a body extending along a longitudinal axis between a first end and an opposite second end, the body having an external surface comprising a plurality of circumferential ridges located between the first end and the second end and extending annularly about the longitudinal axis;
   a reentrant bore extending inwardly from the first end of the body and defining a first cavity;
   the first cavity at least partially bounded by a terminus contained within the body, the terminus intersecting the longitudinal axis;
   a first electrically conductive surface forming a first portion of the external surface, the first electrically conductive surface extending annularly around a first portion of a first circumferential ridge of the plurality of circumferential ridges at a first longitudinal location along the longitudinal axis;
   a second electrically conductive surface forming a second portion of the external surface, the second electrically conductive surface extending annularly around a second portion of the first circumferential ridge of the plurality of circumferential ridges at the first longitudinal location; and
   a power source disposed in the first cavity;
   wherein the first electrically conductive surface is in electrical communication with a first pole of the power source and the second electrically conductive surface is in electrical communication with a second pole of the power source.

2. A device according to claim 1, wherein the body at least partially comprises an hourglass shape.

3. A device according to claim 1, wherein the first electrically conductive surface is disposed on a first plurality of the circumferential ridges.

4. A device according to claim 3, wherein the second electrically conductive surface is disposed on a second plurality of the circumferential ridges.

5. A device according to claim 4, wherein the first plurality of the circumferential ridges is the same as the second plurality of the circumferential ridges.

6. A device according to claim 5, wherein the external surface comprises an electrically insulative portion disposed between the first electrically conductive surface and the second electrically conductive surface.

7. A device according to claim 6, wherein the electrically insulative portion is formed from an elastomeric material having a first durometer hardness and the first and second electrically conductive surfaces having a second durometer hardness.

8. A device according to claim 7, wherein the first durometer hardness is substantially the same as the second durometer hardness.

9. A device according to claim 1, the body extending longitudinally along a length between the first end and the second end, wherein the first cavity extends through the first end and towards the second end, the device further comprising a second cavity extending through the second end towards the first end, the first cavity and the second cavity being separated by a divider forming the terminus of the first cavity.

10. A device according to claim 9, wherein one of the first cavity and the second cavity is longer than one half of the length.

11. A device according to claim 1, wherein when the first conductive surface and the second conductive surface are electrically coupled through a load resistance of up to about 70 kilo-ohms, an electrical current of between 50 microamps and 500 microamps will flow through the load resistance.

12. A device according to claim 11, wherein the electrical current is about 50 microamps to about 250 microamps.

13. A device according to claim 12, wherein the electrical current is about 100 microamps.

14. A device according to claim 1, wherein the power source is housed within an electronics module.

15. A device according to claim 14, wherein the electronics module is water-tight.

16. A device according to claim 14, wherein the electronics module comprises electrical conductors configured to make contact with the first and second electrically conductive surfaces from within the first cavity.

17. A device according to claim 16, wherein the contact between the electrical conductors of the electronics module and the first and second electrically conductive surfaces is frictional.

* * * * *